United States Patent
Okamoto et al.

(10) Patent No.: US 6,603,035 B1
(45) Date of Patent: Aug. 5, 2003

(54) METHOD FOR PRODUCING HIGH PURITY CYANATE

(75) Inventors: Satoshi Okamoto, Ibaraki (JP); Hisashi Watabu, Hyogo (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/377,744

(22) Filed: Aug. 20, 1999

(30) Foreign Application Priority Data

Aug. 20, 1998 (JP) ............................................. 10-234105

(51) Int. Cl.$^7$ ..................... C07C 255/00; C07C 261/00; C07C 43/20; C07D 207/452; C07D 207/444
(52) U.S. Cl. ...................... 558/389; 549/531; 548/521; 548/549; 560/301; 568/654
(58) Field of Search ................... 548/521, 549; 549/531; 558/389; 560/301; 568/654

(56) References Cited

U.S. PATENT DOCUMENTS

| | | |
|---|---|---|
| 3,553,244 A | 1/1971 | Grigat et al. |
| 3,740,348 A | 6/1973 | Grigat et al. |
| 3,755,402 A | 8/1973 | Grigat et al. |
| 4,028,393 A | 6/1977 | Rottloff et al. ............ 560/301 |
| 4,981,994 A | 1/1991 | Jackson |
| 5,420,342 A | 5/1995 | Craig, Jr. |
| 5,932,762 A | 8/1999 | Falchetto et al. |

FOREIGN PATENT DOCUMENTS

| | | |
|---|---|---|
| JP | 41-1928 A | 2/1941 |
| JP | 7-53497 A | 2/1995 |
| JP | 8-92192 A | 4/1996 |

*Primary Examiner*—Alan L. Rotman
*Assistant Examiner*—Taylor V Oh
(74) *Attorney, Agent, or Firm*—Fitch, Even, Tabin & Flannery

(57) ABSTRACT

Provided is a method for producing high purity cyanate derived from a phenol compound represented by the following formula (I):

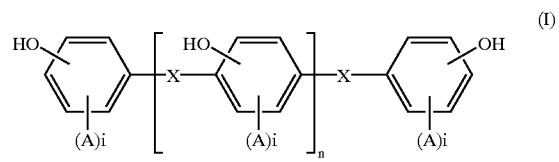

in the formula, each of A independently represents a hydrogen atom or an alkyl group having 1 to 6 carbon atoms, X represents a single bond, an organic group having 1 to 20 carbon atoms, a carbonyl group, a sulfone group, a divalent sulfur atom or an oxygen atom, i and n represent an integer from 0 to 4.

The cyanate contains low amount of impurities such as unreacted phenols and imidecarbonate, and is preferably used as a thermosetting resin for a sealing, laminate, composite material, molding material and adhesive for electric parts.

7 Claims, No Drawings

METHOD FOR PRODUCING HIGH PURITY CYANATE

BACKGROUND OF THE INVENTION

1. Field of the Invention

The present invention relates to a method for producing a thermosetting aromatic cyanate useful as a sealing, laminate, composite material, molding material and adhesive for electric parts.

2. Description of the Related Art

As a method for producing an aromatic cyanate, there has been known a method in which a cyanogen halide is reacted with a phenol compound in the presence of a tertiary aliphatic amine (Japanese Patent Application Publication (JP-B) No. 41-1920).

A thermosetting aromatic cyanate used for electric parts and adhesives desirably have no volatility, therefore, a cyanate derived from a phenol compound having two or more aromatic rings are preferable.

In JP-B NO. 60-52696 and JP-A No. 3-66653, cyanates derived from bisphenols are exemplified, however, the concentration of the bisphenols is as remarkably low as less than 20%.

In the viewpoint of industrial productivity, although a process using a phenol compound in high concentration is desirable, a production method which can produce a high purity cyanate in high yield has not been reported.

SUMMARY OF THE INVENTION

An object of the present invention is to provide a process for producing a high purity aromatic cyanate in high yield, in which a tertiary amine and a cyanogen halide are reacted with a phenol compound with high selectivity at a practical high concentration of the phenol compound.

The present inventors have intensively studied a method for producing an aromatic cyanate, and as a result have found that a high purity aromatic cyanate can be obtained by conducting the reaction in a specific agitating condition, and completed the present invention.

Namely, the present invention relates to a method for producing a high purity cyanate, wherein a phenol compound represented by the following general formula (I):

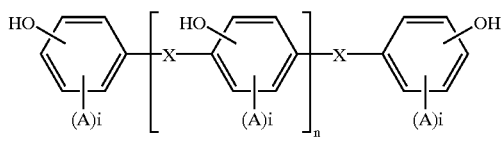

(wherein, each of A independently represents a hydrogen atom or an alkyl group having 1 to 6 carbon atoms, X represents a single bond, an organic group having 1 to 20 carbon atoms, a carbonyl group, a sulfone group, a divalent sulfur atom or oxygen atom, i and n represent an integer from 0 to 4) is reacted with a cyanogen halide in the presence of a tertiary amine and a water-immiscible organic solvent in a reaction vessel equipped with an agitator. The concentration of the phenol compound (the overall charged amount of phenol compound are divided by the sum of the overall charged amount of phenol compound and the overall charged amount of an organic solvent, shown in terms of percentage) is 20 to 50%, and the value of $n \times d^{3/4}$ is 8 or more (here, n is the rotational speed [rpm] and d is the diameter of an impeller [m]).

DETAILED DESCRIPTION OF THE INVENTION

Example of the phenol compounds (I) include 4,4'-dihydroxydiphenyl, 3,3',5,5'-tetramethyl-4,4'-dihydroxydiphenyl, bis(4-hydroxyphenyl)methane, bis(4-hydroxy-3-methylphenyl)methane, bis(4-hydroxy-3-t-butylphenyl)methane, bis(4-hydroxy-3-i-propylphenyl)methane, bis)4-hydroxy-3,5-dimethylphenyl)methane, bis(2-hydroxy-3-t-butyl-5-methylphenyl)methane, bis(4-hydroxyphenyl)ethane, his(4-hydroxy-3-methylphenyl)ethane, bis(4-hydroxy-3-t-butylphenyl)ethane, bis(4-hydroxy-3-i-propylphenyl)ethane, bis(4-hydroxy-3,5-dimethylphenyl)ethane, bis(2-hydroxy-3-t-butyl-5-methylphenyl)ethane, 2,2-bis(4-hydroxyphenyl)propane, 2,2-bis(4-hydroxy-3-methylphenyl)propane, 2,2-bis(4-hydroxy-3-t-butylphenyl)propane, 2,2-bis(4-hydroxy-3-i-propylphenyl)propane, 2,2-bis(4-hydroxy-3,5-dimethylphenyl)propane, 2,2-bis(2-hydroxy-3-t-butyl-5-methylphenyl)propane, 2,2-bis(4-hydroxy-3-t-butyl-6-methylphenyl)propane, 2,2-bis(3-allyl-4-hydroxyphenyl)propane, 1,1-bis(4-hydroxyphenyl)butane, 1,1-bis(4-hydroxy-3-methylphenyl)butane, 1,1-bis(4-hydroxy-3-t-butylphenylbutane, 1,1-bis(4-hydroxy-3-i-propylphenyl)butane, 1,1-bis(4-hydroxy-3,5-dimethylphenyl)butane, 1,1-bis(2-hydroxy-3-t-butyl-5-methylphenyl)butane, 1,1-bis(4-hydroxy-3-t-butyl-6-methylphenyl)butane, 2,2-bis(3-allyl-4-hydroxyphenyl)propane, 1,1-bis(3-allyl-4-hydroxyphenyl)butane, 1,1-bis(4-hydroxyphenyl)cyclohexene, 1,1-bis(4-hydroxy-3-methylphenyl)cyclohexane, bis(4-hydroxyphenyl)sulfide, bis(4-hydroxy-3-methylphenyl)sulfide, bis(4-hydroxy-3-t-butylphenyl)sulfide, bis(4-hydroxy-3-i-propylphenyl)sulfide, bis(4-hydroxy-3,5-dimethylphenyl)sulfide, bis(2-hydroxy-3-t-butyl-5-methylphenyl)sulfide, bis(4-hydroxyphenyl)sulfone, bis(4-hydroxy-3-methylphenyl)sulfone, bis(4-hydroxy-3-t-butylphenyl)sulfone, bis( 4--hydroxy-3-i-propylphenyl)sulfone, bis(4-hydroxy-3,5-dimethylphenyl)sulfone, bis(2-hydroxy-3-t-butyl-5-methylphenyl)sulfone, bis(4-hydroxyphenyl)ether, bis(4-hydroxy-3-methylphenyl)ether, bis(4-hydroxy-3-t-butylphenyl)ether, bis(4-hydroxy 3-i-propylphenyl)ether, bis(4-hydroxy-3,5-dimethylphenyl)ether, bis(2-hydroxy-3-t-butyl-5-methylphenyl)ether, bis(4-hydroxyphenyl)carbonyl, bis(4-hydroxy-3-methylphenyl)carbonyl, bis(4-hydroxy-3-t-butylphenyl)sulfide, bis(4-hydroxy-3-i-propylphenyl)carbonyl, bis(4-hydroxy-3,5-dimethylphenyl)carbonyl, bis(2-hydroxy-3-t-butyl-5-methylphenyl)carbonyl and the like. Among them, bis(4-hydroxyphenyl)methane, bis(4-hydroxy-3,5-dimethylphenyl)methane, 2,2-bis(4-hydroxyphenyl)propane, 2,2-bis(4-hydroxy-3,5-dimethylphenyl)propane are preferable, and 2,2-bis(4-hydroxyphenyl)propane is further preferable.

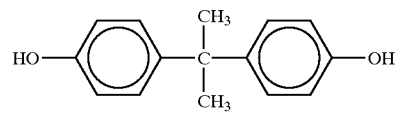

The reaction in conducted by dissolving a phenol compound in an organic solvent, then contacting and mixing a cyanogen halide with the phenol solution by mixing together with a tertiary amine, or by previously mixing a phenol compound, a tertiary amine and a water-immiscible organic solvent and then contacting and mixing a cyanogen halide with the resulting mixed solution.

The organic solvent is immiscible with water, and includes: ketones such as methyl ethyl ketone, methyl isobutyl ketone and the like; aromatic hydrocarbons such as benzene, toluene, xylene and the like; ethers such as diethyl ether, tetrahydrofuran and the like; halogenated hydrocarbons such as methylene chloride, chloroform, carbon tetrachloride, chlorobenzene and the like; nitriles such as benzonitrile and the like; nitro compounds such as nitrobenzene and the like; and esters such as ethyl acetate, ethyl benzoate and the like.

In the case of an aromatic hydrocarbon which does not dissolve a phenol compound, it is preferable that the phenol compound is previously mixed and dissolved by using a tertiary amine then is contacted with a cyanogen halide, and toluene is particularly preferably used as an aromatic hydrocarbon solvent.

In the case of a solvent which dissolves a phenol compound, the phenol compound is dissolved in a solvent, then a tertiary amine and a cyanogen halide are contacted with the solution, however, it is more preferable that the phenol compound is previously mixed and dissolved by using a tertiary amine then a cyanogen halide is contacted with the solution since a dialkylcyanamide which is by-produced by the reaction of a cyanogen halide with a tertiary amine is suppressed. Ketones are suitably used, and among them methylisobutyl ketone is preferable.

When a phenol compound is previously mixed and dissolved in an organic solvent in the presence of a tertiary amine, it may be advantageous that the phenol compound is apparently dissolved completely. When dissolution is difficult, heating may be conducted under condition that a tertiary amine does not vaporize. When a phenol compound is not dissolved, selectivity of the reaction may decrease.

The tertiary amine is not particularly restricted, and examples thereof include trimethylamine, triethylamine, tripropylamine, tributylamine, dimethylethylamine, tribenzylamine, dimethylaniline, diethylaniline and the like. The amount used thereof is from 1.0 to 3-fold equivalent based on hydroxyl groups in a phenol compound, and preferably from 1.0 to 2.0-fold equivalent for enhancing conversion to a cyanate.

As the cyanogen halide, cyanogen chloride or cyanogen bromide is used, and in the case of cyanogen chloride, the reaction temperature is from −40 to 4° C., more preferably from −10 to 30° C. for more safe handling, and in the case of cyanogen bromide, the reaction temperature is from −40 to 65° C. The amount used of a cyanogen halide is from 1.0 to 3-fold equivalent based on hydroxy groups in a phenol compound, and preferably from 1.0 to 2.0-fold equivalent for enhancing conversion to a cyanate. For suppressing by-production of a dialkylcyanamide, the amount of tertiary amine (equivalent based on hydroxyl groups in a phenol compound) is desirably the same or less of that of a cyanogen halide.

The concentration of the phenol compound is given by dividing the overall charged amount of phenol compound by the sum of the overall charged amount of phenol compound and the overall charged amount of an organic solvent and expressed in terms of percentage.

It is preferable that the concentration of a phenol compound is 20% or more for contributing the improvement of reactivity. However, a solution having a concentration of 50% or more of a phenol compound has increased viscosity, and can not be mixed uniformly. The concentration is preferably in the range of from 20% to 40%.

The form of an impeller is not particularly restricted, and any of a propeller, a paddle, a turbine, a Pfaudler, an anchor, a max blend and the like may be used, and an anchor and a Pfaudler are generally used in chemical industry.

In the reaction of the present invention, agitating is carried out in the condition of $n \times d^{3/2}$ is 8 or more. Here, the diameter d at an impeller may be represented by a diameter of an orbital circle drawn by tip of the blade. The rotational speed n is measured in terms of stirring number per one minute [rpm].

The upper limit of $n \times d^{3/2}$ is not especially limited, but it is usually 1000 or less, preferably 500 or less, and further preferably 300 or less.

There is no restriction regarding the use of a baffle plate, however, it is preferably amounted for accelerating mixing providing the strength of a reaction vessel and/or a baffle plate is in the permissible range.

The post treatment and purification method after completion of the reaction are not particularly restricted. For example, as shown in JP-A No. 8-92192, a hydrochloride salt of a tertiary amine is removed by water washing, an organic solvent is partially distilled off, then crystallization is conducted with using a solvent such as alcohol and the like, thus impurities can be removed efficiently.

EXAMPLES

The following examples illustrate the present invention, but do not limit the scope of the present invention.

Example 1

In a beaker, 255.0 g of 2,2'-bis(4-hydroxyphenyl)propane (manufactured by Mitsiui Chemicals Inc.), 248.7 g of triethylamine (manufactured by Daicel Chemical Industries, Ltd.), and 255.0 g of toluene (manufactured by Mitsubishi Chemical Corporation) were dissolved, and it was visually recognized that there were no insolubles.

127 ml of cyanogen chloride and 340 g of toluene were charged into a reaction vessel equipped with a Pfaudler impeller of 60 mm diameter and a thermometer, and the reaction vessel was cooled. Into the reaction vessel was added the above-described solution containing 2,2'-bis(4-hydroxyphenyl)propane dropwise over about 2 hours at a rotational speed of 600 rpm taking care to keep the temperature of the mixture at 10° C. or lower. After the addition, the mixture was stirred for 30 minutes at 10° C. or lower. Here, $n \times d^{3/2}$ was 8.82 and the concentration of the phenol compound in the solution to which all the raw materials had been charged was 30%.

The reaction solution was washed with 40° C. water (total of 595 g, 3 times) to obtain a toluene solution of a crude product. The resulted toluene solution was analyzed by liquid chromatography to find that the reaction yield of 2,2'-bis(4-cyanatephenyl)propane was 96.1%, the reaction yield of 2-(4-cyanatephenyl)-2'-(4-hydroxyphenyl)propane was 0.6%, and the reaction yield of 2,2'-bis(4-hydroxyphenyl)propane was 0.2%.

Comparative Examples 1 and 2, Examples 2 to 6

Comparative examples and examples are summarized in Table 1 below. Conditions other than conditions shown in Table 1 are as described in Example 1. Results are analyzed values by liquid chromatography of toluene solutions.

In Comparative Examples 1 and 2, relatively much amount of the unreacted phenol remained, and an imide carbonate (φ—O—C(=NH)—O—φ) was produced as a by-product, therefore, a high purity cyanate could not be obtained.

TABLE 1

| Item | Comparative example 1 | Comparative example 2 | Example 2 | Example 3 | Example 4 | Example 5 | Example 6 |
|---|---|---|---|---|---|---|---|
| Reaction condition | | | | | | | |
| BPA [kg] | 0.150 | 0.150 | 0.255 | 7.50 | 300 | 0.150 | 0.255 |
| Solvent | Toluene | MIBK | Toluene | Toluene | Toluene | MIBK | Toluene |
| Amount of solvent [kg] | 0.500 | 0.500 | 0.500 | 17.50 | 970 | 0.602 | 0.589 |
| Concentration of phenol [%] | 23 | 23 | 30 | 30 | 24 | 20 | 30 |
| Form of impeller | Pfaudler | Pfaudler | Pfaudler | Pfaudler | Anchor | Pfaudler | Anchor |
| n: Rotational speed [x $\mu$m] | 400 | 400 | 800 | 180 | 75 | 600 | 680 |
| d: Diameter of impeller [m] | 0.06 | 0.06 | 0.06 | 0.3 | 1.3 | 0.06 | 0.08 |
| n x $d^{3/2}$ | 5.87 | 5.87 | 11.8 | 29.6 | 111 | 8.82 | 15.4 |
| Result | | | | | | | |
| Yield [%] | 70.4 | 89.4 | 98.4 | 98.8 | 95.2 | 95.0 | 99.0 |
| Mono cyanate [%] | 8.0 | 12.1 | 1.0 | 1.1 | 2.0 | N.D. | N.D. |
| MPA [%] | 0.3 | 2.1 | 0.2 | N.D. | N.D. | N.D. | N.D. |

BPA: 2,2'-bis(4-hydroxyphenyl)propane (manufactured by Mitsui Chemicals Inc.)
Toluene: toluene (manufactured by Mitsubishi Chemical Corporation)
MIBK: methyl isobutyl ketone (manufactured by Wako Pure Chemical Industries, guaranteed reagent)
Mono cyanate: 2-(4-cyanotephenyl)-2'-(4-hydroxyphenyl)propane
N.D.: Not detected by liquid chromatography An aromatic cyanate produced by the method of the present invention is used as a thermosetting resin for a sealing, laminate, composite material, molding material and adhesive for electric parts.

According to the present invention, it is possible to produce a high purity aromatic cyanate in high concentration which is even industrially practical.

What is claimed is:

1. A method for producing a high purity cyanate comprising reacting a phenol compound represented by the following formula (I):

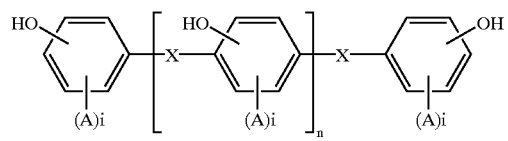

wherein each A independently represents a hydrogen atom or an alkyl group having 1 to 6 carbon atoms, x represents a single bond, an organic group having 1 to 20 carbon atoms, a carbonyl group, a sulfone group, a divalent sulfur atom or an oxygen atom, i and n represent an integer from 0 to 4, with a cyanogen chloride at a temperature from $-10°$ C. to $30°$ C. in the presence of a tertiary amine which is triethylamine, triethylamine, tripropylamine, tributylamine, dimethylethylamine, tripropylamine, tributylamine, dimethylethylamine, tribenzylamine, dimethylaniline or diethylaniline and a water-imiscible organic solvent in a reaction vessel equipped with an agitator under the condition that: the concentration of the phenol compound, shown in terms of percentage where the overall charged amount of the phenol compound is divided by the sum of the overall charged amount of the phenol compound and the overall charged amount of an organic solvent, is 20 to 50%; and the value of (n) x $d^{2/3}$ is 8 or more, where the rotational speed is n (rpm) and the diameter of an impeller is d (m).

2. The method according to claim 1, wherein the impeller is an anchor or a Pfaudler.

3. The method according to claim 1, wherein the phenol compound is bis (4-hydroxphenyl) methane, bis(4-hydroxy-3,5-dimethylphenyl)methane, 2,2-bis(4-hydroxphenyl)propane, or 2,2-bis(4-hydroxy-3,5-dimethylphenyl)propane.

4. The method according to claim 1, wherein the teritary amine is used in an amount of 1.0 to 2.0 equivalent based on hydroxyl groups of the phenol compound.

5. The method according to claim 1, wherein the cyanogen chloride is used in the equivalent amount of the tertiary amine or more.

6. The method according to claim 1, wherein the water-immiscible organic solvent is an aromatic hydrocarbon or a ketone compound.

7. The method according to claim 1 or 6, wherein the water-immiscible organic solvent is toluene or methylisobutylketone.

* * * * *